US009616899B2

(12) United States Patent
Sprock et al.

(10) Patent No.: US 9,616,899 B2
(45) Date of Patent: Apr. 11, 2017

(54) SYSTEM AND METHOD FOR WORKSITE OPERATION OPTIMIZATION BASED ON OPERATOR CONDITIONS

(71) Applicant: Caterpillar Inc., Peoria, IL (US)

(72) Inventors: Christopher Sprock, East Peoria, IL (US); Michael Hatfield, Peoria, IL (US); Timothy Crane, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/641,324

(22) Filed: Mar. 7, 2015

(65) Prior Publication Data

US 2016/0257310 A1 Sep. 8, 2016

(51) Int. Cl.
| | |
|---|---|
| G08B 23/00 | (2006.01) |
| B60W 40/08 | (2012.01) |
| G08B 7/00 | (2006.01) |
| G06Q 10/06 | (2012.01) |
| G06Q 50/08 | (2012.01) |

(52) U.S. Cl.
CPC .......... B60W 40/08 (2013.01); G06Q 10/063 (2013.01); G06Q 50/08 (2013.01); G08B 7/00 (2013.01); *B60W 2040/0827* (2013.01); *B60W 2040/0872* (2013.01); *B60W 2540/22* (2013.01); *B60W 2540/26* (2013.01); *B60W 2710/30* (2013.01)

(58) Field of Classification Search
CPC ............ G07C 5/00; G07C 5/008; G07C 5/02; G07C 5/08; G07C 5/0816; B60W 40/08; G08B 7/00; G06Q 10/063; G06Q 50/08
USPC .................................. 340/576, 439; 701/50
See application file for complete search history.

(56) References Cited

U.S. PATENT DOCUMENTS

| | | | |
|---|---|---|---|
| 6,313,749 B1 * | 11/2001 | Horne | .................... G08B 21/06 340/575 |
| 6,734,799 B2 | 5/2004 | Munch | |
| 6,927,694 B1 * | 8/2005 | Smith | .................. B60K 28/066 340/573.1 |
| 6,946,966 B2 | 9/2005 | Koenig | |
| 7,027,621 B1 | 4/2006 | Prokoski | |
| 8,125,529 B2 * | 2/2012 | Skoskiewicz | ............ G08G 1/04 348/116 |
| 8,139,108 B2 | 3/2012 | Stratton et al. | |
| 8,485,822 B2 | 7/2013 | Lind | |
| 8,725,311 B1 | 5/2014 | Breed | |
| 8,872,640 B2 | 10/2014 | Horseman | |
| 2007/0038354 A1 | 2/2007 | Kang | |

(Continued)

FOREIGN PATENT DOCUMENTS

| | | |
|---|---|---|
| WO | 2013006642 | 1/2013 |
| WO | 2013066380 | 5/2013 |

*Primary Examiner* — Thomas Mullen
(74) *Attorney, Agent, or Firm* — Miller, Matthias & Hull (57) ABSTRACT

Systems and methods for optimizing worksite operations based on operator conditions are disclosed. One method includes receiving first data including one or more of a worksite model and information relating to actual operation of a worksite, wherein the worksite model includes a simulated operation of a machine associated with the worksite. Second data may be received, the second data associated with an operator of a machine at the worksite and including one or more of nutritional data, health data, and sleep data. An operation state may be determined based at least on the first data and the second data. A response may be generated based at least on the determined operation state.

20 Claims, 6 Drawing Sheets

(56) References Cited

U.S. PATENT DOCUMENTS

2010/0063652 A1 3/2010 Anderson
2013/0070043 A1 3/2013 Geva et al.
2014/0266739 A1 9/2014 Chen

* cited by examiner

SYSTEM AND METHOD FOR WORKSITE OPERATION OPTIMIZATION BASED ON OPERATOR CONDITIONS

TECHNICAL FIELD

This disclosure relates generally to worksite operations involving heavy machinery, and more particularly to a system and method for optimizing the operation of a worksite based on operator conditions.

BACKGROUND

A worksite, such as a mining or construction site, will typically include a variety of machines, such as bulldozers, excavators, dump trucks, and the like, working cooperatively to accomplish a particular task. In order to accomplish the task efficiently, the operation, availability, and mechanical status of the machines may be tracked and coordinated to ensure that each machine is used to its maximum benefit. For example, if a worksite included an excavator filling dump trucks with material, a shortfall of dump trucks would result in the excavator sitting idly while waiting for an empty dump truck to receive the excavated material. Another important factor in coordinating the machines for optimal efficiency is the status of the machine operators themselves. For instance, if an operator is sleep-deprived, he or she will likely not operate his or her machine optimally and, thus, negatively impact the coordination of the machines and the overall efficiency of the worksite.

U.S. Pat. No. 7,027,621 discloses a method and apparatus for operator condition monitoring and assessment. The disclosed method and apparatus uses passive infrared imaging of the face and other body parts of an operator to surmise the condition of the operator. The disclosed method and apparatus do not, however, address how the condition of the operator may affect the coordination and overall efficiency of a worksite in which the operator is working.

SUMMARY

This disclosure relates to system and methods for optimizing the operation of a worksite based on operator conditions. In an aspect, a method may include receiving first data including one or more of a worksite model and information relating to actual operation of a worksite, wherein the worksite model includes a simulated operation of a machine associated with the worksite. Second data may be received, the second data associated with an operator of a machine at the worksite and including one or more of nutritional data, health data, and sleep data. An operation state may be determined based at least on the first data and the second data. A response may be generated based at least on the determined operation state.

In an aspect, a system may include a processor and a memory bearing instructions that, upon execution by the processor, cause the system at least to receive a first data. The first data may include one or more of a worksite model and information relating to actual operation of a worksite, wherein the worksite model includes a simulated operation of a machine associated with the worksite. Second data may be received, the second data associated with an operator of a machine at the worksite and including one or more of nutritional data, health data, and sleep data. An operation state may be determined based at least on the first data and the second data. A response may be generated based at least on the determined operation state.

In an aspect, a computer readable storage medium may bear instructions that, upon execution by a processor, effectuate operations including receiving first data including one or more of a worksite model and information relating to actual operation of a worksite, wherein the worksite model includes a simulated operation of a machine associated with the worksite. Second data may be received, the second data associated with an operator of a machine at the worksite and including one or more of nutritional data, health data, and sleep data. An operation state may be determined based at least on the first data and the second data. A response may be generated based at least on the determined operation state.

BRIEF DESCRIPTION OF THE DRAWINGS

The following detailed description is better understood when read in conjunction with the appended drawings. For the purposes of illustration, examples are shown in the drawings; however, the subject matter is not limited to the specific elements and instrumentalities disclosed. In the drawings.

DETAILED DESCRIPTION

The systems and methods of the disclosure may leverage operator condition components such as health condition components and hardware to monitor the condition of an operator in real time and understand the operator's current state and future state from the information provided. As an example, the systems and methods may monitor specific operator nutrition and biological factors, including vital signs, nutrition levels, sleep levels, and heart rate. As another example, the methods and systems may be used to make adjustments and improvements in real time in anticipation of correcting future operator performance problems or conditions that have yet to manifest. As a further example, the systems and methods may be utilized in conjunction with an existing site simulator to optimize the operation of a site such as a worksite.

Figure 1:
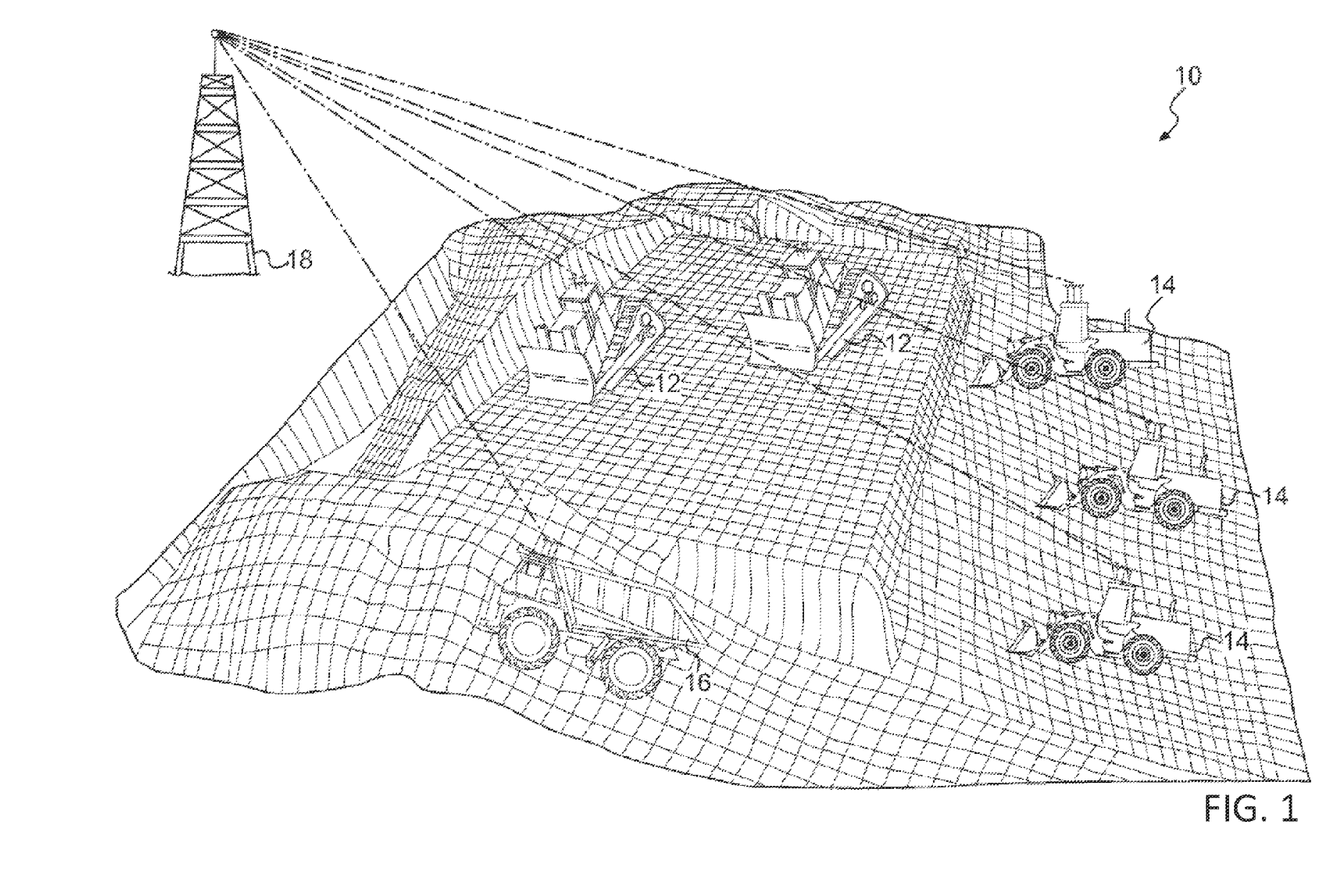
FIG. 1 illustrates an exemplary worksite in accordance with aspects of the disclosure.

FIG. 1 shows a worksite 10 such as, for example, an open pit mining operation. As part of the mining function, various machines may operate at or between different locations of the worksite 10. These machines may include, one or more digging machines 12, one or more loading machines 14, one or more hauling machines 16, one or more transport machines (not shown), and/or other types of machines known in the art. Each of the machines at the worksite 10 may be in communication with each other and with a central station 18 by way of wireless communication to remotely transmit and receive operational data and instructions.

The digging machine 12 may refer to any machine that reduces material at the worksite 10 for the purpose of subsequent operations (e.g., for blasting, loading, and hauling operations). Examples of the digging machines 12 may include excavators, backhoes, dozers, drilling machines, trenchers, drag lines, etc. Multiple digging machines 12 may be co-located within a common area at worksite 10 and may perform similar functions. As such, under normal conditions, similar co-located digging machines 12 should perform about the same with respect to productivity and efficiency when exposed to similar site conditions.

The loading machine 14 may refer to any machine that lifts, carries, and/or loads material that has been reduced by the digging machine 12 onto waiting hauling machines 16. Examples of the loading machine 14 may include a wheeled or tracked loader, a front shovel, an excavator, a cable shovel, a stack reclaimer, or any other similar machine. One or more loading machines 14 may operate within common areas of the worksite 10 to load reduced materials onto the hauling machines 16. Under normal conditions, similar co-located loading machines 14 should perform about the same with respect to productivity and efficiency when exposed to similar site conditions.

The hauling machine 16 may refer to any machine that carries the excavated materials between different locations within the worksite 10. Examples of the hauling machine 16 may include an articulated truck, an off-highway truck, an on-highway dump truck, a wheel tractor scraper, or any other similar machine. Laden hauling machines 16 may carry overburden from areas of excavation within the worksite 10, along haul roads to various dump sites, and return to the same or different excavation areas to be loaded again. Under normal conditions, similar co-located hauling machines 16 should perform about the same with respect to productivity and efficiency when exposed to similar site conditions.

Figure 2:
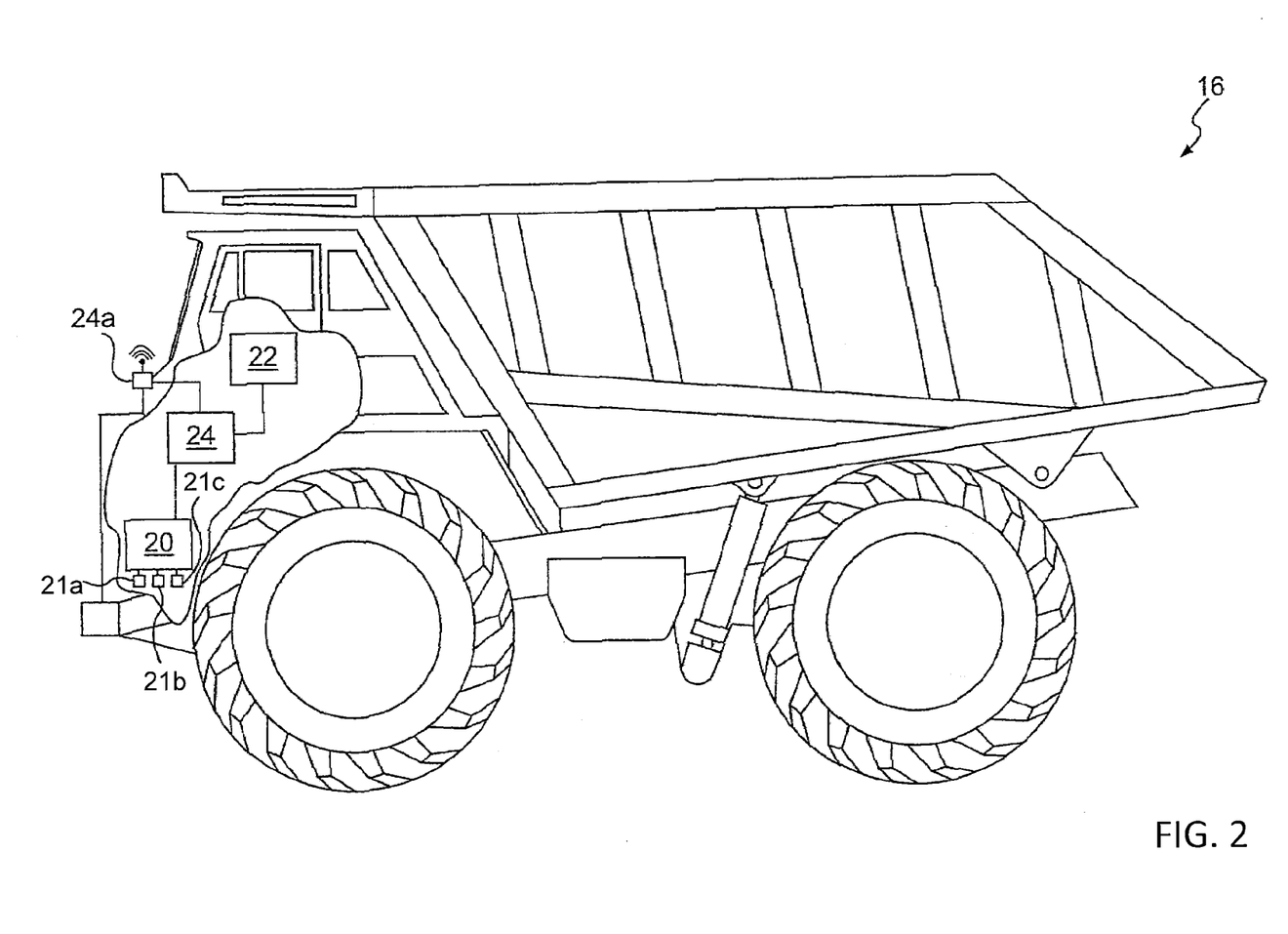
FIG. 2 illustrates a schematic side view of an exemplary machine in accordance with aspects of the disclosure.

FIG. 2 shows one exemplary machine that may be operated at the worksite 10. It should be noted that, although the depicted machine may embody the hauling machine 16, the following description may be equally applied to any machine operating at the worksite 10. The hauling machine 16 may record and transmit data to the central station 18 (referring to FIG. 1) during its operation on a communication channel is defined herein. Similarly, the central station 18 may analyze the data and transmit information to the hauling machine 16 on a communication channel defined herein. The data transmitted to the central station 18 may include operator data, machine identification data, performance data, worksite data, diagnostic data, and other data, which may be automatically monitored from onboard the hauling machine 16 and/or manually observed and input by machine operators. The information remotely transmitted back to the hauling machines 16 may include electronic terrain maps, machine configuration commands, instructions, recommendations and/or the like.

Identification data may include machine-specific data, operator-specific data, location-specific data and/or the like. Machine-specific data may include identification data associated with a type of machine (e.g., digging, loading, hauling, etc.), a make and model of machine (e.g., Caterpillar 797 OHT), a machine manufacture date or age, a usage or maintenance/repair history, etc. Operator-specific data may include an identification of a current operator, information about the current operator (e.g., a skill or experience level, an authorization level, an amount of time logged during a current shift, a usage history, etc.), a history of past operators, operator health and biological characteristics (e.g., vital signs, nutrition levels, sleep levels, and heart rate), etc. Site-specific data may include a task currently being performed by the operator, a current location at the worksite 10, a location history, a material composition at a particular area of the worksite 10, a site-imposed speed limit, etc.

Performance data may include current and historic data associated with operation of any machine at the worksite 10. Performance data may include, for example, payload information, efficiency information, productivity information, fuel economy information, speed information, traffic information, weather information, road and/or surface condition information, maneuvering information (e.g., braking, steering, wheel slip, etc.), downtime and repair or maintenance information, etc.

Diagnostic data may include recorded parameter information associated with specific components and/or systems of the machine. For example, diagnostic data may include engine temperatures, engine pressures, engine and/or ground speeds and acceleration, fluid characteristics (e.g., levels, contamination, viscosity, temperature, pressure, etc.), fuel consumption, engine emissions, braking conditions, transmission characteristics (e.g., shifting, torques, and speed), air and/or exhaust pressures and temperatures, engine calibrations (e.g., injection and/or ignition timings), wheel torque, rolling resistance, system voltage, etc. Some diagnostic data may be monitored directly, while other data may be derived or calculated from the monitored parameters. Diagnostic data may be used to determine performance data, if desired.

To facilitate the collection, recording, and transmitting of data from the machines at the worksite 10 to the central station 18 (referring to FIG. 1) and vice versa, each of the hauling machines 16 may include an onboard control module 20, an operator interface module 22, and a communication module 24. The communication module 24 may communicate over a communication channel as defined herein. Data received by the control module 20 and/or the operator interface module 22 may be sent offboard to the central station 18 by way of the communication module 24. The communication module 24 may also be used to send instructions and/or recommendations from the central station 18 to an operator of the hauling machine 16 by way of the operator interface module 22. It is contemplated that additional or different modules may be included onboard the hauling machine 16, if desired.

The control module 20 may include a plurality of sensors 21*a*, 21*b*, 21*c* distributed throughout hauling machine 16 and/or the operator and configured to gather data from the operator and/or various components and subsystems of the hauling machine 16. It is contemplated that a greater or lesser number of sensors may be included than that shown in FIG. 2.

In an aspect, the sensors 21*a-c* may include any device that senses, detects, or measures a condition of a machine operator. The sensors 21*a-c* may be directed toward sensing an operator condition relating to the operator's general health status. For example, such a health status sensor may include a heart rate monitor, a blood pressure monitor, a breathing-rate monitor, a pulse oximeter, a body temperature monitor, a sensor to measure the amount of an operator's sweat production or the like. One or more of the sensors 21*a-c* may monitor an operator condition relating to the operator's state of alertness, restfulness, tiredness, and so on. For example, the control module 20 may include an eye monitor to detect eye movements, eye fixation points, blink rates, eye closures or the like which each may be indicative of an operator with waning alertness. As another example, the control module 20 may include a biometric monitor capable of detecting and recording the amount, quality, and patterns of an operator's sleep. A facial movement monitor may detect movement of an operator's head or facial features, such as the head nodding preceding a lapse into a sleep state. The control module 20 may monitor a condition relating to an operator's nutritional status. For instance, the control module 20 may include a blood-sugar monitor, which may indicate that an operator has not eaten for an extended period of time. As another example, the control module 20 may monitor the number of calories that an operator has burned over a period of time.

It should be appreciated that the control module 20 and/or a component thereof (e.g., sensors 21a-c) may be integrated with the hauling machine 16, may be worn by or attached to an operator of the hauling machine 16 or a combination thereof. For example, the control module 20 may include a wrist-worn biometric sensing device wirelessly coupled (utilizing a communication channel as defined herein) with a smart phone on the operator's person. The wrist-worn biometric sensing device may detect an operator's heart rate, sleep activity, and physical activity, for example, and transmit them to the smart phone for storage, organization, and analysis. Furthermore, the control module 20 may be worn by the operator while the operator is not currently operating the hauling machine 16. For example, the control module 20 that monitors sleep activity may be worn by the operator during the night preceding a work shift and the resulting sleep activity data may be used to optimize the worksite.

In another aspect, the sensors 21a-c may be associated with a power source (not shown), a transmission (not shown), a traction device, a work implement, an operator station, and/or other components and subsystems of the hauling machine 16. These sensors may be configured to provide data gathered from each of the associated components and subsystems. Other pieces of information may be generated or maintained by data control module 20 such as, for example, time of day, date, weather, road or surface conditions, and machine location (global and/or local).

The control module 20 may also be in direct communication with the separate components and subsystems of the hauling machine 16 to facilitate manual, autonomous, and/or remote monitoring and/or control of the hauling machine 16. For example, control module 20 may be in communication with the power source of the hauling machine 16 to control fueling, the transmission to control shifting, a steering mechanism to control heading, a differential lock to control traction, a braking mechanism to control deceleration, a tool actuator to control material dumping, and with other components and/or subsystems of the hauling machine 16. Based on direct commands from a human operator, remote commands from the central station 18 or another one of the machines 12, 14, 16 at the worksite 10, and/or self-direction, the control module 20 may selectively adjust operation of the components and subsystems of the hauling machine 16 to accomplish a predetermined task.

The operator interface module 22 may be located onboard the hauling machine 16 for collection and/or recording of data. The operator interface module 22 may include or be communicatively connected to one or more operator data input devices such as a pressable button, a movable dial, a keyboard, a touchscreen, a touchpad, a pointing device, or any other means by which an operator may indicate an aspect of his or her condition. For example, the operator interface module 22 may include a touchpad, which may be used by the operator to move a cursor on a display screen, such as an LCD screen, to select an indicator of the operator's condition. As examples of data that an operator may input to the operator interface module 22, the operator may type in the time that the operator's last meal was consumed or the number of consecutive hours that the operator has been awake. Other examples may include the time of the operator's last break (from which an elapsed time may thus be calculated) or a self-assessed indication of the operator's level of tiredness (e.g., by a selection of a value on a scale of one to ten). The operator interface module 22 may be integrated with the hauling machine 16 or may, instead, be unattached from the hauling machine 16 and disposed adjacent the operator, such as being worn by an operator. For example, the operator interface module 22 may be embodied in a smartphone through which an operator may input data relating to his or her condition. The operator interface module 22 may be communicatively connected to the central station 18, in addition to or alternatively to the connection to the control module 20.

The data received via the operator interface module 22 may include observed information associated with the worksite 10, the hauling machine 16, and/or the operator. For example, the observed data may include a defect in the road over which hauling machine 16 is passing, an amount of observed precipitation or visibility at the worksite 10, an excessive vibration, sound, or smell of the hauling machine 16, and/or operator information such as identity, start time, health information, nutrition information, and/or operator sleep information. The operator may record this information into a physical or electronic log book (not shown) located within the hauling machine 16 during or after a work shift or such information may be automatically collected or modelled. In some cases, data from the operator interface module 22 may automatically be combined with data captured by the control module 20. For example, operator input regarding a type and criticality of a road defect may be coordinated with a geographical location of the hauling machine 16, a vibration measured at the time that the observed data was input, and the name of the operator driving the hauling machine 16 at the time the defect was encountered and the sleep and nutrition patterns of the operator before and during the time that the observed data was input. Such operator information may be used to determine what effect the operator condition has on the information collected and/or to detect an irregularity in site operations, an inefficiency in site operations, and/or an operator warning condition (such as a detection that the operator is experiencing micro-sleep events).

The communication module 24 may include any device that facilitates communication of data between the hauling machine 16 and the central station 18, and/or between the machines 12, 14, 16. The communication module 24 may include hardware and/or software that enables sending and/or receiving data through a wireless communication link 24a. It is contemplated that, in some situations, the data may be transferred to the central station 18 and/or other machines 12, 14, 16 through a direct data link (not shown), or downloaded from the hauling machine 16 and uploaded to the central station 18, if desired. It is also contemplated that, in some situations, the data automatically monitored by the control module 20 may be electronically transmitted, while the operator-observed data may be communicated to the central station 18 by a voice communication device, such as a two-way radio (not shown).

The communication module 24 may also have the ability to record the monitored and/or manually-input data. For example, the communication module 24 may include a data recorder (not shown) having a recording medium (not shown). In some cases, the recording medium may be portable, and data may be transferred from the hauling machine 16 to the central station 18 or between the machines 12, 14, 16 using the portable recording medium.

Figure 3:
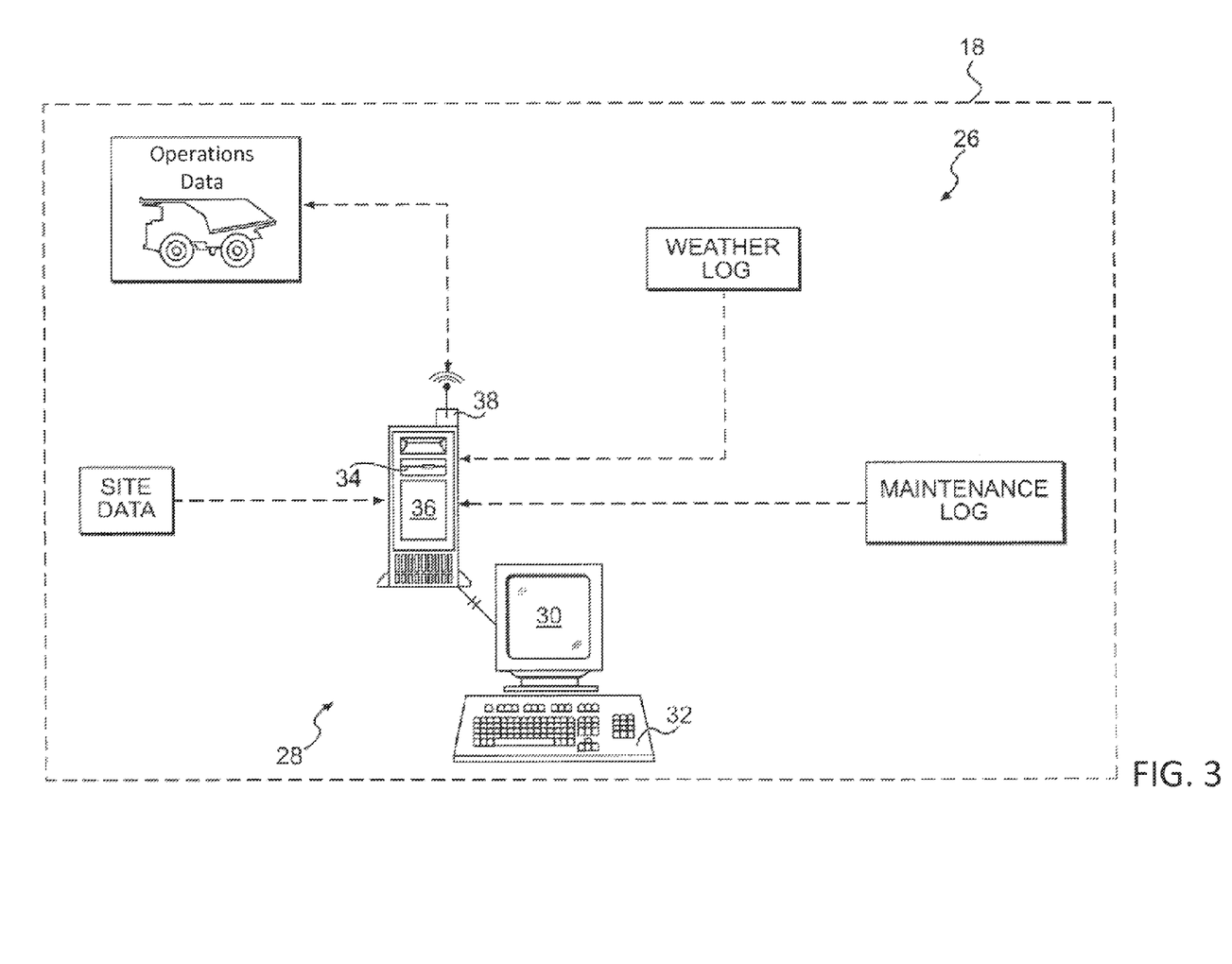
FIG. 3 illustrates a block diagram of an exemplary data flow in accordance with aspects of the disclosure.

FIG. 3 is a schematic illustration of a worksite management system 26 configured to receive and analyze the data communicated to the central station 18 from the machines 12, 14, 16 and from other sources (e.g., operators). The worksite management system 26 may include an offboard controller 28 in remote communication with the machines 12, 14, 16 via the central station 18 and configured to process data from a variety of sources and execute management methods at the worksite 10. For the purposes of this disclosure, the controller 28 may be primarily focused at positively affecting performance irregularities and/or warning conditions experienced by the operators and/or the machines 12, 14, 16 operating at the worksite 10. Positively affecting may include reducing a likelihood of occurrence, reducing a magnitude of the irregularity, reducing a frequency of the irregularity, reducing a severity of the irregularity, minimizing inefficiencies, identifying contributors to error, or otherwise improving machine and/or worksite operation associated with the irregularity.

The controller 28 may include any type of computer or a plurality of computers networked together. The controller 28 may be located proximate the mining operation of the worksite 10 or may be located at a considerable distance remote from the mining operation, such as in a different city or even a different country. It is also contemplated that computers at different locations may be networked together to form the controller 28, if desired. In one aspect, the controller 28 may be located onboard one or more of the machines 12, 14, 16 at the worksite 10, if desired.

The controller 28 may include among other things, a console 30, an input device 32, an input/output device 34, a storage media 36, and a communication interface 38. The console 30 may be any appropriate type of computer display device that provides a graphical user interface (GUI) to display results and information to operators and other users of the worksite management system 26. The input device 32 may be provided for operators to input information into the controller 28. The input device 32 may include, for example, a keyboard, a mouse, or another computer input device. The input/output device 34 may be any type of device configured to read/write information from/to a portable recording medium. The input/output device 34 may include among other things, a floppy disk, a CD, a DVD, a flash memory read/write device or the like. The input/output device 34 may be provided to transfer data into and out of the controller 28 using a portable recording medium. The storage media 36 could include any means to store data within the controller 28, such as a hard disk. The storage media 36 may be used to store a database containing among others, historical worksite, machine, and operator related data. The communication interface 38 may provide connections with the central station 18, enabling the controller 28 to be remotely accessed through computer networks, and means for data from remote sources to be transferred into and out of the controller 28. The communication interface 38 may contain network connections, data link connections, and/or antennas configured to receive wireless data.

Data may be transferred to the controller 28 electronically or manually. Electronic transfer of data may include the remote transfer of data using the wireless capabilities or the data link of the communication interface 38 by a communication channel as defined herein. Data may also be electronically transferred into the controller 28 through a portable recording medium using the input/output device 34. Manually transferring data into the controller 28 may include communicating data to a control system operator in some manner, who may then manually input the data into the controller 28 by way of, for example, the input device 32. The data transferred into the controller 28 may include machine identification data, performance data, diagnostic data, and other data. The other data may include for example, weather data (current, historic, and forecast), machine maintenance and repair data, site data such as survey information or soil test information, and other data known in the art.

The controller 28 may generate an analysis of the data collected from the control modules of each machine 12, 14, 16 at the worksite 10 and present results of the analysis to a user of the worksite management system 26 and/or to the operators of particular machines 12, 14, 16 thereof by way of the communications interface 38, for example. The results may include a productivity analysis, an economic analysis (e.g., efficiency, fuel economy, operational cost, etc.), a cycle time analysis, an environmental analysis (e.g., engine emissions, road conditions, site conditions, etc.), or other analysis specific to each machine, each category of machines (i.e., for the digging machines 12, for the loading machines 14, or for the hauling machines 16), each co-located machine, each operator associated with the machines 12, 14, 16, and/or for the worksite 10 as a whole. In one aspect, results of the analysis may be indexed according to time, for example, according to a particular shift, a particular 24-hr period, or another suitable parameter (e.g., time period, liters of fuel, cost, etc.).

The results of the analysis may be in the form of detailed reports or they may be summarized as a visual representation such as, for example, with an interactive graph. The results may be used to show a historical performance, a current performance, and/or an anticipated performance of the operators or the machines 12, 14, 16 operating at the worksite 10. Alternatively or additionally, the results could be used to predict a progression of operations at the worksite 10 and to estimate a time before the productivity, efficiency, or other performance measure of a particular machine, operator, group of machines, or the worksite 10 becomes irregular (i.e., exceeds or falls below a desired or expected limit). As an example, the results of the analysis may indicate when a performance irregularity has occurred, is currently occurring, or anticipated to occur in the future. The controller 28 may flag the user of the worksite management system 26 at the time of the irregularity occurrence or during the analysis stage when the irregularity is first detected and/or anticipated.

For the purposes of this disclosure, a performance irregularity can be defined as a non-failure deviation from a historical, expected, or desired machine or worksite performance (e.g., productivity, efficiency, emission, traffic congestion, or similar related performance) that is monitored, calculated, or otherwise received by the worksite management system 26 or other system. In one aspect, an amount of deviation required for the irregularity classification may be set by a machine operator, a user of the worksite management system 26, a business owner, or other responsible entity. In some situations, the performance irregularity may be indicative of a site condition over which little control may be exercised, but that may still be accommodated to improve operations at the worksite 10.

Based on the analysis, when a performance irregularity has been determined to have occurred, be currently occurring, or is anticipated to occur, the controller 28 may be configured to remotely reconfigure an operational relationship of particular machines 12, 14, 16 and thereby positively affect the performance irregularity. The operational relationship may be associated with, for example, the shift points included within a transmission map, engine valve and/or ignition timings included within an engine calibration map, fuel settings included within a torque limit map, maximum or minimum speed limits included within a travel limit map, steering boundaries included within a steering map, pressure and/or priority settings included within a tool actuation map, or other similar settings, limits, and/or boundaries contained within other software maps, algorithms, and/or equations stored electronically within the memory of the control module 20. In general, reconfiguring the operational relationships described above may affect how a particular machine 12, 14, 16 responds to different situations. For example, reconfiguring the shift points of a transmission map may control the engine speed and/or wheel torques at which a transmission of a particular machine 12, 14, 16 shifts to a lower or higher gear combination. Similarly, changing engine valve and/or ignition timings of an engine calibration map may control under what conditions intake and/or exhaust valves open or close, at what point within an engine cycle the combustion gas is energized, and resulting engine cylinder pressures and emissions. These changes to the operational relationships of the hauling machine 16 may be implemented to improve productivity, efficiency, and emissions, or otherwise positively affect the performance irregularity, and may be maintained within the software maps, algorithms, and/or equations until a subsequent reconfiguration is implemented. In other words, reconfiguration of a machine's operational relationship may be semi-permanent and affect subsequent machine performance for an extended period of time. Examples of reconfiguration implementation will be provided in the following section.

Figure 4:
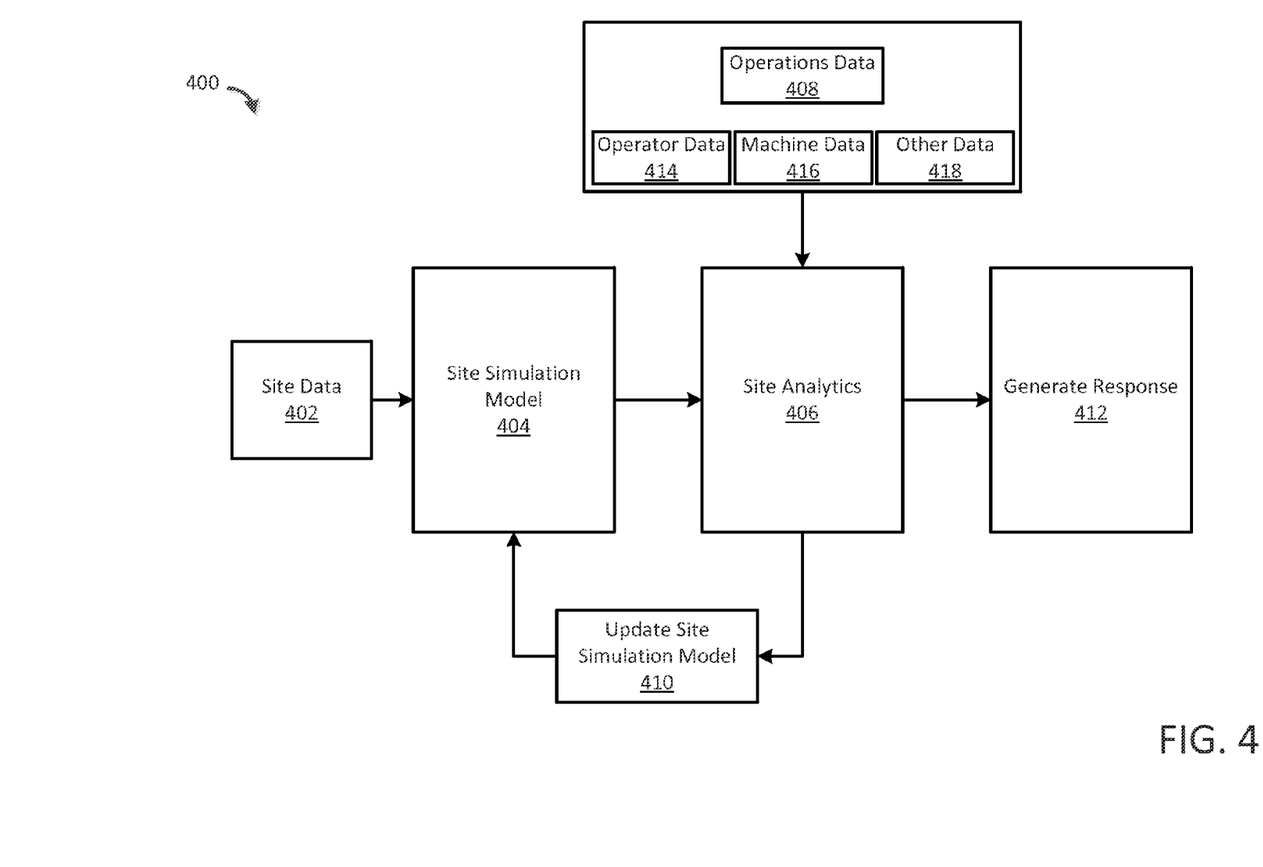
FIG. 4 illustrates a block diagram of an exemplary data flow in accordance with aspects of the disclosure.

FIG. 4 depicts an exemplary flow diagram 400 of various operations relating to a method to optimize worksite operations based on operator conditions. In an aspect, at module 404, a site simulation model may be accessed, received, and/or generated. The site simulation model may simulate the operations of a worksite, including one or more operations of a machine (e.g., machines 12, 14, 16 (FIG. 1)). For example, and referring back to the exemplary worksite 10 depicted in FIG. 1, the site simulation model may simulate the operation of the loading machine 14 depositing a material into the hauling machine 16. The site simulation model may, in turn, simulate the laden hauling machine 16 traveling along a road and unloading its payload to a processing machine, wherein the delivered material is simulated being processed. The site simulation model may then simulate the empty hauling machine 16 traveling back over the road to repeat the process. The site simulation may be determined by the controller 28 or other processor. For example, the site simulation may be determined at a server or other processor controlled by a third-party and subsequently delivered to and received by the controller 28.

The site simulation model of module 404 may be based on site data 402 (e.g., worksite data). The site data 402 may include information on the layout and planning of the worksite 10. This may include the locations of material, a processing machine, and one or more roads. Additionally, information on the layout of the worksite 10 may include the location of a dump zone, a scale, a loadout or the like.

The site data 402 may include performance information such as information relating to the theoretical or projected performance characteristics of the machines operating at the worksite 10. As examples, performance information may include a projected loading rate of the loading machine 14 (e.g., tons loaded per hour), a projected processing rate of a processing machine (e.g., tons processed per hour), a projected carrying capacity of the hauling machine 16 (e.g., tons of material per load), a projected maximum safe travel speed of the hauling machine 16 or the like. Performance information may also include projected performance metrics relating to the cooperative operation of more than one machine 12, 14, 16. For example, performance information may include the projected amount of time that the loading machine 14 should take to fill the bed of a particularly-sized hauling machine 16. As another example, performance information may include the projected cycle time of a complete cycle of the loading machine 14 filling the hauling machine 16, the hauling machine 16 delivering its payload to a processing machine, and the hauling machine 16 returning again to the loading machine 14.

The site data 402 may include information pertaining to the roads of the worksite 10. For example, this may include information on the material composition of a road (e.g., paved, dirt, mud or the like). Road information may also include the weight-bearing capacity of a road (e.g., 100 tons), the maximum speed at which machines 12, 14, 16 may safely operate on a road, or a metric indicating the level of deterioration of a road. The site data 402 may include a designation of a hauling route over one or more roads.

The site data 402 may include cost-related information. Cost-related information may include a purchase cost of a machine 12, 14, 16, a lease cost of a machine 12, 14, 16, an operating cost of a machine 12, 14, 16 (e.g., fuel, wear-and-tear deterioration) or the like. Other cost-related information may include wage costs for personnel associated with the worksite 10, including those personnel operating the machines 12, 14, 16. Cost-related information may additionally include road construction cost, road maintenance cost, and power costs such as for electricity or natural gas. As a further example, the site data 402 may include information pertaining to site goals. For example, site goal information may include a goal cost of operation or a goal productivity level (e.g., a particular amount of material processing in a specified period of time).

In module 406, site analytics may be performed. The site analytics may be performed based on the site simulation model determined in the module 404 and the operations data 408. The operations data 408 may include operator data 414, machine data 416, and/or other data 418. The operations data 408 may be transmitted to and received by the central station 18 (FIG. 3) or other computer or processor.

The operator data 414 may be any information pertaining to a condition of an operator. The operator data 414 may include data received from the control module 20 and/or an electronic device (e.g., a smart phone) coupled with the control module 20. An operator sensing device (e.g., the control module 20, the sensors 21*a-c*, etc.) may be associated with the operator (e.g., it is worn by the operator both while operating and not operating the machine) or the machine 12, 14, 16 that the operator is operating (e.g., it is attached to or integrated with the machine 12, 14, 16). Examples of the operator data 414 deriving from an operator sensing device may include heart rate, blood pressure, rate of breath, blood-oxygen level, skin temperature, body temperature, galvanic skin response, sweat production, sleep status, microsleep occurrence, eye movement, head movement, facial movement, yawn occurrence, pupil dilation, eye fixation point, blink rate, eye closure, sleep activity, blood-sugar level, and caloric expenditure data. The operator data 414 from an operator sensing device may represent real-time data, historical data, or a combination thereof.

The operator data 414 may be derived from data input by an operator via the control module 20 and/or the operator interface module 22. Examples of operator data 414 include recent eating activity, recent sleep activity, an elapsed time that an operator has been awake, or a self-assessed indication of an operator's level of tiredness or other condition.

Operator data 414 may additionally include previously-known data retrieved from storage of the central station 18 or other connected storage. Previously-known data may include biographical operator data, such as age, gender, and experience level. It may include scheduling information relating to an operator, such as the number of consecutive days that the operator has worked.

Machine data 416 may include any information pertaining to the operation of a machine 12, 14, 16. Machine data 416 may be input from the sensors 21*a-c*. Examples of machine data 416 gathered from the sensors 21*a-c* include operator manipulation of the input devices, tool, or power source, machine velocity, machine location, fluid pressure, fluid flow rate, fluid temperature, fluid contamination level, fluid viscosity, electric current level, electric voltage level, fluid (e.g., fuel, water, oil) consumption rates, payload level, payload value, percent of maximum allowable payload limit, payload history, payload distribution, transmission output ratio, cycle time, idle time, grade, recently performed maintenance, or recently performed repair.

Machine data 416 may additionally include empirical performance information, similar to that of site data 402 but instead based on actual measurements from the sensors 21*a-c* or other sources. For example, empirical performance information may include an actual loading rate of the loading machine 14, an actual processing rate of a processing machine, an actual carrying capacity of the hauling machine 16, or an actual maximum safe travel speed of the hauling machine 16. As with the site data 402, empirical performance information may include empirical performance metrics relating to the cooperative operation of more than one machine 12, 14, 16. As an example, empirical performance information may include the actual cycle time of the hauling machine 16 accepting a load, delivering that load, and returning for another load.

Other data 418 may include updated road information, such as real-time data on a road condition (e.g., an indication that a road is muddy, has suffered new damage, or is blocked). Other data 418 may further include an indication of an accident involving a machine 12, 14, 16.

Referring back to module 406, site analytics are performed. Site analytics may be performed that identify a current inefficiency, predict a future inefficiency, or identify a recreated historical inefficiency at the worksite 10, each based on the site simulation model of module 404 and/or the operations data 408. An inefficiency may relate to any aspect of the operations of the worksite 10 and may include an exceeding of a pre-specified threshold relating to that aspect. As used herein, exceeding of a pre-specified threshold may refer to either a numerical aspect being greater than a pre-specified threshold or less than a pre-specified threshold, according to the context of usage. Examples of an inefficiency may include an indication that the hauling machines 16 are sitting idle for a time period exceeding a threshold (e.g., longer than one minute) while waiting for the loading machine 14 to finish loading its current load or an indication that the hauling machines 16 on a road are traveling below a threshold relating to their maximum safe speed (e.g., less than twenty miles per hour) due to traffic congestion on the road. Other examples may include an indication that the worksite 10 is processing less material than projected, an indication that a machine 12, 14, 16 is consuming more fuel than projected, or an indication that the hauling machine 16 is having a longer loading/unloading cycle time than projected. Note that the aforementioned examples apply equally in the predictive sense, e.g., predicting that the hauling machines 16 will sit idle, and in the historical sense, e.g., identifying that the hauling machines 16 were sitting idle. Site analytics may additionally include identifying a factor which may contribute to or may have contributed to an identified current inefficiency, an identified future inefficiency, or an identified historical inefficiency. For example, if an identified inefficiency includes an indication that the hauling machine 16 is sitting idle while waiting for the loading machine 14 for a period beyond a pre-specified threshold, the site analytics may identify a factor contributing to the idleness, such as the loading machine 14 operator suffering from instances of microsleep or low blood-sugar, which thus cause the loading machine 14 operator to perform slowly. In the preceding examples, the instances of microsleep or low blood-sugar may be identified by an exceeding of a pre-specified threshold (e.g., more than three instances of microsleep per minute or less than seventy milligrams per deciliter, respectively).

In an aspect, site analytics may identify a current inefficiency. For example, operations data 408, including operator data 414 from an operator sensing device, such as a movement detector, and machine data 416, may indicate instances of an operator's head nodding and the load times of the loading machine 14. The site analytics may identify an inefficiency and a factor relating to that inefficiency by identifying that the load times are below a threshold and by identifying that the number of operator head nods is exceeding a threshold (thus indicating tiredness).

In an aspect, site analytics may identify and predict a future inefficiency. As an example, operator data 414 from an operator sensing device, such as a blood-sugar monitor, may indicate that an operator has a blood-sugar level below a threshold, perhaps from having gone too long without eating. The site analytics may identify and predict that the operator's machine 12, 14, 16 will perform at sub-standard level, such as low loading times or low hauling cycle times. As another example, operator data 414 in which an operator indicated that he or she received only a small amount of sleep the prior night and indicated a high self-assessed level of tiredness may be used in the site analytics. The site analytics may identify and predict that the operator may be prone to cause an accident at the worksite 10 and thus negatively impact one or more aspects of the worksite's operation.

In an aspect, site analytics may identify a historical inefficiency such as in a recreation of the operations of the worksite 10. As an example, stored operations data 408 may indicate that an accident occurred with the hauling machine 16. The site analytics may identify that the cycle time of the hauling machine 16 sharply declined subsequent to the accident. Site analytics may additionally identify a factor which may have contributed to an identified inefficiency. Continuing the accident example, the operations data 408 used in the site analytics may include an indication from an operator sensing device that the operator underwent a number of instances of microsleep in the time period shortly preceding the accident that exceeds a threshold. Accordingly, the indication of microsleeps may be a factor that contributed to the accident, i.e., the operator may have fallen asleep while operating the machine 12, 14, 16 and thus caused the accident.

The site analytics may be performed by the central station 18. Additionally, the site analytics may instead be performed by any other server or processor, such as a third-party server at a separate location, and subsequently transmitted to the central station 18.

In module 410, the site simulation model may be updated based on the site analytics of module 406. This may include transmitting operations data 408, which was not included in the previous site simulation model, back to module 404 for incorporation into an updated site simulation model. This may additionally include transmitting an inefficiency or factor contributing to an inefficiency identified in the site analytics of module 406 to module 404 so that the inefficiency or factor may be incorporated into an updated site simulation model.

In module 412, a response is generated based on the site analytics of module 406. A response may be generated and further transmitted by the central station 18, for example. A response may include an instruction relating to an inefficiency identified in module 406. An instruction may be delivered to a machine 12, 14, 16 operator or other personnel at the worksite 10, such as a foreman or supervisor. An instruction may include an electronic communication (e.g., email, short message service (SMS) text message, or text file) and may be delivered from the central station 18 to a display system of a machine 12, 14, 16. An instruction relating to an inefficiency may include, for example, an instruction for an operator to take a rest break based on site analytics having determined an inefficiency relating to the tiredness or microsleep occurrences of the operator. As another example, an instruction relating to an inefficiency may include an instruction for an operator to eat a meal or snack. Such instruction may be based on site analytics which determined an inefficiency relating to, for example, low blood-sugar of the operator or an indication of hunger by the operator.

A generated response may include a warning, for example, to an operator. The warning may be transmitted to a display system (of a machine 12, 14, 16), which may be embodied in a digital display, one or more warning lights, or an audio alarm, for example. A warning may include a visual indicator such as a message or icon to be displayed on a display system and directed towards an operator or other personnel at the worksite 10. For example, if the site analytics determined an inefficiency relating to an operator's blood-sugar level, a warning that the operator's performance may, be impaired may be generated and delivered to a display system of the operator's machine 12, 14, 16. As another example, if the site analytics determined an inefficiency relating to an operator's tiredness, a warning including an instruction to light a warning light and/or sound an audible indicator, such as an audio alarm, may be generated and delivered to a display system of the operator's machine 12, 14, 16. An instruction or warning may include a variable level of severity. To illustrate, if a machine 12, 14, 16 approaches a dangerous portion of a road, the site analytics of module 406 may predict a possible inefficiency based on the dangerous portion (e.g., a possible accident) and a low-severity warning to the operator may be provided, such as a small warning light or a message on a display system. However, if a machine 12, 14, 16 approaches the same dangerous portion of the road and the site analytics also identifies an inefficiency relating to the operator's tiredness, a high-severity warning to the operator may be provided, such as bright flashing lights or a loud audio alarm.

INDUSTRIAL APPLICABILITY

The industrial applicability of the system and methods for worksite operation optimization based on an operator condition herein described will be readily appreciated from the foregoing discussion. Although various machines 12, 14, 16 are described in relation to FIG. 1, those skilled in the art may understand that the machine 12, 14, 16 is not so limited and may include any manner of work vehicle or equipment that may be found at a worksite. Similarly, although the hauling machine 16 is depicted in FIG. 2, any type of work vehicle or equipment may be used.

Conventionally, a worksite may be optimized according to factors relating directly to the mechanical operation of the machines and the physical layout of the worksite. However, such conventional systems do not take into account operator conditions, such as operator tiredness, health, or nutritional deficiencies. When operator conditions are included in site analytics, worksite inefficiencies and factors contributing to those inefficiencies may be more effectively identified and addressed in a subsequent response.

Figure 5:
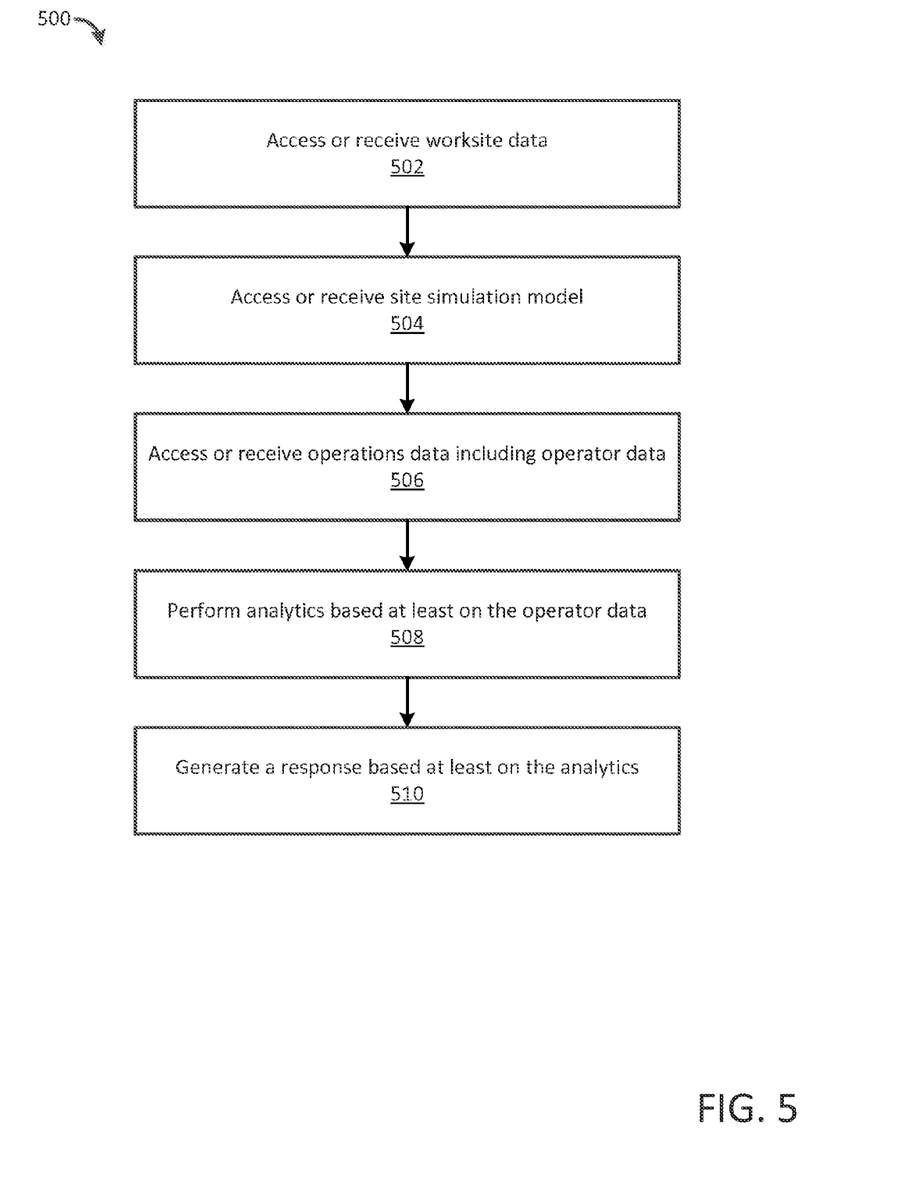
FIG. 5 illustrates a flow chart of an exemplary method in accordance with aspects of the disclosure.

FIG. 5 illustrates a process flow chart for a method 500 for worksite operation optimization based on an operator condition. For illustration, the operations of the method 500 will be discussed in reference to FIGS. 1, 2, and 3. At step 502, site data 402 may be received. As an example, site data 402 may be received by a central station 18. Site data 402 may be previously stored on the central station 18 or may be received from another server or processor, including one associated with a third party. Site data 402 may include theoretical or projected performance characteristics of machines 12 operating at the worksite 10 (e.g., a projected loading rate of the loading machine 14) or performance characteristics of machines 12 operating in conjunction (e.g., a cycle time of the loading machine 14 loading the hauling machine 16, the hauling machine 16 traveling to a processing machine, and the processing machine receiving the hauling machine's 110 payload). Site data 402 may include data on a road of the worksite 10, such as the material composition, layout, weight-bearing capacity, maximum speed, or a metric indicating a level of deterioration of the road. Site data 402 may additionally include cost-related data, such as the purchase or lease cost of a machine 12, 14, 16, wage costs for operators or other personnel, road costs, or power costs. Site data 402 may include site goal data, such as a goal for cost of operation or productivity level for the worksite 10.

At step 504, a site simulation model may be received that simulates the operations of the worksite 10, including a machine 12, 14, 16 operation. The site simulation model may be received by the central station 18, for example, after the site simulation model is determined based, at least in part, on site data 402. The determination of the site simulation model may be performed by the central station 18 or another processor, including one controlled by a different party than that controlling the central station 18.

At step 506, operations data 408 may be received by, for example, the central station 18. The operations data 408 may include operator data 414, machine data 416, or other data 418.

Operator data 414 may be any information pertaining to a condition of a machine 12, 14, 16 operator (e.g., nutrition, health, sleep, or tiredness). Examples of operator data 414 include heart rate, blood pressure, rate of breath, blood-oxygen level, skin temperature, body temperature, galvanic skin response, sweat production, sleep status, microsleep occurrence, eye movement, head movement, facial movement, yawn occurrence, pupil dilation, eye fixation point, blink rate, eye closure, sleep activity, blood-sugar level, and caloric expenditure data. Further examples include recent eating activity, recent sleep activity, the elapsed time that an operator has been awake, or a self-assessed indication of an operator's level of tiredness or other condition. Operator data 414 may be transmitted from an operator sensing device or an operator data input device.

Machine data 416 may include any information pertaining to the operation of a machine 12, 14, 16 transmitted from sensors 21*a-c*. Examples of machine data 416 from sensors 21*a-c* include operator manipulation of the input devices, tool, or power source, machine velocity, machine location, fluid pressure, fluid flow rate, fluid temperature, fluid contamination level, fluid viscosity, electric current level, electric voltage level, fluid (e.g., fuel, water, oil, DEF, coolant) consumption rates, payload level, payload value, percent of maximum allowable payload limit, payload history, payload distribution, transmission output ratio, cycle time, idle time, grade, recently performed maintenance, or recently performed repair. Machine data 416 may additionally include empirical performance information, such as an actual loading rate of the loading machine 14, an actual processing rate of a processing machine, an actual carrying capacity of the hauling machine 16, or an actual maximum safe travel speed of the hauling machine 16.

Other data 418 may include updated road information, such as real-time data on a road condition (e.g., an indication that a road is muddy, has suffered new damage, or is blocked). Other data 418 may additionally include an indication of an accident involving a machine 12, 14, 16. An indication of an accident may be transmitted from a machine sensing device capable of detecting a collision or other type of vehicle accident.

At step 508, site analytics are performed by, for example, the central station 18. The site analytics may be performed based on received operations data 408 and at least one of: received site data 402, a received site simulation model, or a combination thereof. Site analytics may include identifying a current inefficiency, predicting a future inefficiency, or identifying a historical inefficiency at the worksite 10. An inefficiency may relate to an aspect of the operations of the worksite 10 and may be determined by data (e.g., operations data 408) relating to that aspect exceeding a pre-specified threshold. Examples of an inefficiency may include an indication that the hauling machines 16 are sitting idle for a time period exceeding a threshold (e.g., longer than one minute) while waiting for the loading machine 14 to finish loading its current load or an indication that the hauling machines 16 on a road are traveling below a threshold relating to their maximum safe speed (e.g., less than twenty miles per hour) due to traffic congestion on the road. Site analytics may additionally include identifying a factor which may contribute to or may have contributed to an identified current inefficiency, an identified future inefficiency, or an identified historical inefficiency. For example, identifying a factor relating to slow machine 12, 14, 16 performance may include identifying that an operator has suffered a number of instances of microsleep exceeding a threshold.

The site analytics and/or operation data 408 may be used to update the site simulation model. The site analytics and/or operation data 408 may be transmitted to the server or processor that first determined the site simulation model, which may then use the site analytics and/or operations data 408 to determine an updated site simulation model.

At step 510, a response is generated by, for example, the central station 18 based on the site analytics. A response may include an instruction relating to an operator warning condition such as an inefficiency or factor contributing to an inefficiency and may be embodied in an electronic communication such as an email, SMS text message, or text file. The response may be configured to result in a remediation of the operator warning condition. As an example, an instruction to the operator may include, for example, a message for an operator to take a rest break or to eat a meal. A response may also include a warning directed to, for example, an operator. A warning may include an electronic communication such as an email, SMS text, or text file or may include an electronic instruction for a warning light to be lit or an audio alarm to be sounded, for example. As an example, a warning may include a message for a hungry operator to take special care or may include instructions for an alarm to sound to alert a tired operator to an upcoming dangerous portion of a road.

The generated response may further be transmitted to, for example, a display system (e.g., operator interface module 22) of a machine 12, 14, 16, so that the operator may be apprised of an instruction or warning. The response may additionally be transmitted to another electronic device, such as a smartphone, tablet computer, laptop, or personal computer of the operator or other worksite 10 personnel (e.g., foreman or supervisor). The response may be transmitted by, for example, the central station 18.

Whether such functionality is implemented as hardware or software depends upon the design constraints imposed on the overall system. Skilled persons may implement the described functionality in varying ways for each particular application, but such implementation decisions should not be interpreted as causing a departure from the scope of the disclosure. In addition, the grouping of functions within a module, block, or step is for ease of description. Specific functions or steps may be moved from one module or block without departing from the disclosure.

The various illustrative logical blocks and modules described in connection with the aspects disclosed herein may be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the aspects disclosed herein may be embodied directly in hardware, in a software module executed by a processor (e.g., of a computer), or in a combination of the two. A software module may reside, for example, in RAM memory, flash memory, ROM memory, EPROM memory, EEPROM memory, registers, hard disk, a removable disk, a CD-ROM, or any other form of storage medium. An exemplary storage medium may be coupled to the processor such that the processor may read information from, and write information to, the storage medium. In the alternative, the storage medium may be integral to the processor. The processor and the storage medium may reside in an ASIC.

In at least some aspects, a processing system (e.g., control module 20, controller 28, etc.) that implements a portion or all of one or more of the technologies described herein may include a general-purpose computer system that includes or is configured to access one or more computer-accessible media.

Figure 6:
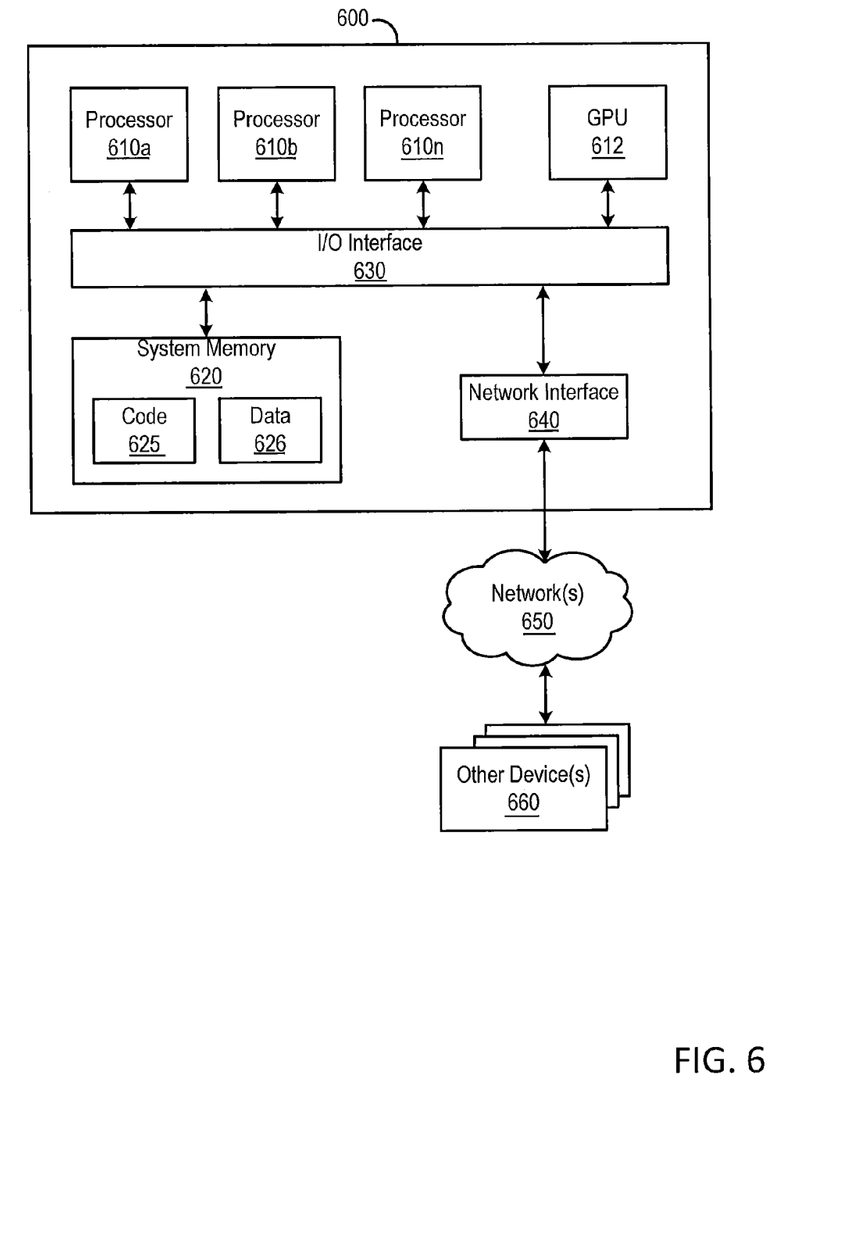
FIG. 6 illustrates a block diagram of a computer system configured to implement the method of FIG. 5.

FIG. 6 depicts a general-purpose computer system that includes or is configured to access one or more computer-accessible media. In the illustrated aspect, a computing device 600 may include one or more processors 610a, 610b, and/or 610n (which may be referred herein singularly as the processor 610 or in the plural as the processors 610) coupled to a system memory 620 via an input/output (I/O) interface 630. The computing device 600 may further include a network interface 640 coupled to an I/O interface 630.

In various aspects, the computing device 600 may be a uniprocessor system including one processor 610 or a multiprocessor system including several processors 610 (e.g., two, four, eight, or another suitable number). The processors 610 may be any suitable processors capable of executing instructions. For example, in various aspects, the processor(s) 610 may be general-purpose or embedded processors implementing any of a variety of instruction set architectures (ISAs), such as the x86, PowerPC, SPARC, or MIPS ISAs, or any other suitable ISA. In multiprocessor systems, each of the processors 610 may commonly, but not necessarily, implement the same ISA.

In some aspects, a graphics processing unit ("GPU") 612 may participate in providing graphics rendering and/or physics processing capabilities. A GPU may, for example, include a highly parallelized processor architecture specialized for graphical computations. In some aspects, the processors 610 and the GPU 612 may be implemented as one or more of the same type of device.

The system memory 620 may be configured to store instructions and data accessible by the processor(s) 610. In various aspects, the system memory 620 may be implemented using any suitable memory technology, such as static random access memory ("SRAM"), synchronous dynamic RAM ("SDRAM"), nonvolatile/Flash®-type memory, or any other type of memory. In the illustrated aspect, program instructions and data implementing one or more desired functions, such as those methods, techniques and data described above, are shown stored within the system memory 620 as code 625 and data 626.

In one aspect, the I/O interface 630 may be configured to coordinate I/O traffic between the processor(s) 610, the system memory 620 and any peripherals in the device, including a network interface 640 or other peripheral interfaces. In some aspects, the I/O interface 630 may perform any necessary protocol, timing or other data transformations to convert data signals from one component (e.g., the system memory 620) into a format suitable for use by another component (e.g., the processor 610). In some aspects, the I/O interface 630 may include support for devices attached through various types of peripheral buses, such as a variant of the Peripheral Component Interconnect (PCI) bus standard or the Universal Serial Bus (USB) standard, for example. In some aspects, the function of the I/O interface 630 may be split into two or more separate components, such as a north bridge and a south bridge, for example. Also, in some aspects some or all of the functionality of the I/O interface 630, such as an interface to the system memory 620, may be incorporated directly into the processor 610.

The network interface 640 may be configured to allow data to be exchanged between the computing device 600 and other device or devices 660 attached to a network or networks 650, such as other computer systems or devices, for example. In various aspects, the network interface 640 may support communication via any suitable wired or wireless general data networks, such as types of Ethernet networks, for example. Additionally, the network interface 640 may support communication via telecommunications/telephony networks, such as analog voice networks or digital fiber communications networks, via storage area networks, such as Fibre Channel SANs (storage area networks), or via any other suitable type of network and/or protocol.

In some aspects, the system memory 620 may be one aspect of a computer-accessible medium configured to store program instructions and data as described above for implementing aspects of the corresponding methods and apparatus. However, in other aspects, program instructions and/or data may be received, sent, or stored upon different types of computer-accessible media. Generally speaking, a computer-accessible medium may include non-transitory storage media or memory media, such as magnetic or optical media, e.g., disk or DVD/CD coupled to computing device the 600 via the I/O interface 630. A non-transitory computer-accessible storage medium may also include any volatile or non-volatile media, such as RAM (e.g., SDRAM, DDR SDRAM, RDRAM, SRAM, etc.), ROM, etc., that may be included in some aspects of the computing device 600 as the system memory 620 or another type of memory. Further, a computer-accessible medium may include transmission media or signals, such as electrical, electromagnetic or digital signals, conveyed via a communication medium, such as a network and/or a wireless link, such as those that may be implemented via the network interface 640. Portions or all of multiple computing devices, such as those illustrated in FIG. 6, may be used to implement the described functionality in various aspects; for example, software components running on a variety of different devices and servers may collaborate to provide the functionality. In some aspects, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

It should also be appreciated that the systems in the figures are merely illustrative and that other implementations might be used. Additionally, it should be appreciated that the functionality disclosed herein might be implemented in software, hardware, or a combination of software and hardware. Other implementations should be apparent to those skilled in the art. It should also be appreciated that a server, gateway, or other computing node may include any combination of hardware or software that may interact and perform the described types of functionality, including without limitation desktop or other computers, database servers, network storage devices and other network devices, PDAs, tablets, cellphones, wireless phones, pagers, electronic organizers, Internet appliances, and various other consumer products that include appropriate communication capabilities. In addition, the functionality provided by the illustrated modules may in some aspects be combined in fewer modules or distributed in additional modules. Similarly, in some aspects the functionality of some of the illustrated modules may not be provided and/or other additional functionality may be available.

Each of the operations, processes, methods, and algorithms described in the preceding sections may be embodied in, and fully or partially automated by, code modules executed by at least one computer or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto may be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example aspects. The example systems and components described herein may be configured differently than described. For example, elements may be added to, removed from, or rearranged compared to the disclosed example aspects.

It will also be appreciated that various items are illustrated as being stored in memory or on storage while being used, and that these items or portions of thereof may be transferred between memory and other storage devices for purposes of memory management and data integrity. Alternatively, in other aspects some or all of the software modules and/or systems may execute in memory on another device and communicate with the illustrated computing systems via inter-computer communication. Furthermore, in some aspects, some or all of the systems and/or modules may be implemented or provided in other ways, such as at least partially in firmware and/or hardware, including, but not limited to, at least one application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the modules, systems and data structures may also be stored (e.g., as software instructions or structured data) on a computer-readable medium, such as a hard disk, a memory, a network, or a portable media article to be read by an appropriate drive or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other aspects. Accordingly, the disclosure may be practiced with other computer system configurations.

Conditional language used herein, such as, among others, "may," "could," "might," "may," "e.g.," and the like, unless specifically stated otherwise, or otherwise understood within the context as used, is generally intended to convey that certain aspects include, while other aspects do not include, certain features, elements, and/or steps. Thus, such conditional language is not generally intended to imply that features, elements, and/or steps are in any way required for at least one aspects or that at least one aspects necessarily include logic for deciding, with or without author input or prompting, whether these features, elements, and/or steps are included or are to be performed in any particular aspect. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example aspects have been described, these aspects have been presented by way of example only, and are not intended to limit the scope of aspects disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of aspects disclosed herein. The accompanying claims and their equivalents are intended to cover such forms or modifications as would fall within the scope and spirit of certain aspects disclosed herein.

The preceding detailed description is merely exemplary in nature and is not intended to limit the disclosure or the application and uses of the disclosure. The described aspects are not limited to use in conjunction with a particular type of machine. Hence, although the present disclosure, for convenience of explanation, depicts and describes particular machine, it will be appreciated that the assembly and electronic system in accordance with this disclosure may be implemented in various other configurations and may be used in other types of machines. Furthermore, there is no intention to be bound by any theory presented in the preceding background or detailed description. It is also understood that the illustrations may include exaggerated dimensions to better illustrate the referenced items shown, and are not consider limiting unless expressly stated as such.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The disclosure may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), Long Term Evolution (LTE), W-CDMA (Wideband Code-Division Multiple Access), Wireless Fidelity (Wi-Fi), Bluetooth, and/or the like, and/or a combination of two or more thereof.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context.

We claim:

1. A method comprising:
receiving, by one or more processors, first data comprising a worksite model, wherein the worksite model comprises a simulated operation of a machine associated with a worksite;
receiving, by the one or more processors, second data associated with an operator of a machine at the worksite, the second data comprising one or more of nutritional data, health data, and sleep data;
determining, by the one or more processors, an operation state based at least on the first data and the second data;
generating a response based at least on the determined operation state; and
updating the worksite model based at least on the generated response.

2. The method of claim 1, further comprising transmitting the response to the operator.

3. The method of claim 1, wherein the second data is received from a sensor integrated with the machine.

4. The method of claim 1, wherein the second data is received from a sensor disposed adjacent the operator.

5. The method of claim 1, wherein the determining the operation state comprises one or more of detecting an irregularity in worksite operations, detecting an inefficiency in worksite operations, and detecting an operator warning condition.

6. The method of claim 1, wherein the determining the operation state comprises detecting an operator warning condition and wherein the response comprises a remediation to the operator warning condition.

7. The method of claim 1, wherein the response comprises one or more of an audible indicator and a visual indicator.

8. The method of claim 1, wherein the first data further comprises information relating to actual operations performed at a worksite.

9. A system comprising:
a processor; and
a memory bearing instructions that, upon execution by the processor, cause the system at least to:
receive first data comprising a worksite model, wherein the worksite model comprises a simulated operation of a machine associated with a worksite;
receive second data associated with an operator of a machine at the worksite, the second data comprising one or more of nutritional data, health data, and sleep data;
determine an operation state based at least on the first data and the second data;
generate a response based at least on the determined operation state; and
update the worksite model based at least on the generated response.

10. The system of claim 9, wherein the second data is received from one or more of a sensor integrated with the machine and a sensor disposed adjacent the operator.

11. The system of claim 9, wherein the determination of the operation state comprises one or more of detecting an irregularity in worksite operations, detecting an inefficiency in worksite operations, and detecting an operator warning condition.

12. The system of claim 9, wherein the determination of the operation state comprises detecting an operator warning condition and wherein the response comprises a remediation to the operator warning condition.

13. The system of claim 9, wherein the response comprises one or more of an audible indicator and a visual indicator.

14. The system of claim 9, wherein the first data further comprises information relating to actual operations performed at a worksite.

15. A non-transitory computer readable storage medium bearing instructions that, upon execution by a processor, effectuate operations comprising:
receiving first data comprising a worksite model, wherein the worksite model comprises a simulated operation of a machine associated with a worksite;
receiving second data associated with an operator of a machine at the worksite, the second data comprising one or more of nutritional data, health data, and sleep data;
determining an operation state based at least on the first data and the second data;
generate a response based at least on the determined operation state; and
update the worksite model based at least on the generated response.

16. The non-transitory computer readable storage medium of claim 15, wherein the second data is received from one or more of a sensor integrated with the machine and a sensor disposed adjacent the operator.

17. The non-transitory computer readable storage medium of claim 15, wherein the determining of the operation state comprises one or more of detecting an irregularity in worksite operations, detecting an inefficiency in worksite operations, and detecting an operator warning condition.

18. The non-transitory computer readable storage medium of claim 15, wherein the determining of the operation state comprises detecting an operator warning condition and wherein the response comprises a remediation to the operator warning condition.

19. The non-transitory computer readable storage medium of claim 15, wherein the response comprises one or more of an audible indicator and a visual indicator.

20. The non-transitory computer readable storage medium of claim 15, wherein the first data further comprises information relating to actual operation performed at the worksite.

* * * * *